(12) United States Patent
Nuotio et al.

(10) Patent No.: US 10,137,451 B2
(45) Date of Patent: Nov. 27, 2018

(54) REACTION VESSEL AND APPARATUS AND METHOD FOR OPENING AND CLOSING A REACTION VESSEL

(71) Applicant: Thermo Fisher Scientific Oy, Vantaa (FI)

(72) Inventors: Vesa Nuotio, Vantaa (FI); Juhani Siidorov, Vantaa (FI); Sami Kukkonen, Vantaa (FI)

(73) Assignee: THERMO FISHER SCIENTIFIC OY, Vantaa (FI)

( * ) Notice: Subject to any disclaimer, the term of this patent is extended or adjusted under 35 U.S.C. 154(b) by 0 days.

(21) Appl. No.: 15/787,347

(22) Filed: Oct. 18, 2017

(65) Prior Publication Data

US 2018/0036734 A1 Feb. 8, 2018

Related U.S. Application Data

(62) Division of application No. 13/820,960, filed as application No. PCT/FI2011/050950 on Oct. 28, 2011, now Pat. No. 9,821,313.
(Continued)

(51) Int. Cl.
*B01L 3/00* (2006.01)
*B01L 9/06* (2006.01)
(Continued)

(52) U.S. Cl.
CPC ............. *B01L 3/523* (2013.01); *B01L 3/5082* (2013.01); *B01L 9/06* (2013.01); *B65D 83/00* (2013.01); *G01N 35/04* (2013.01); *B01L 2200/025* (2013.01); *B01L 2200/0689* (2013.01); *B01L 2200/142* (2013.01); *B01L 2200/18* (2013.01); *B01L 2300/043* (2013.01);
(Continued)

(58) Field of Classification Search
CPC ........... B01L 2200/025; B01L 2200/18; B01L 3/523; B65D 83/00; G01N 2035/0405; G01N 35/025; G01N 35/04; H01J 49/0409; H01J 49/0413
See application file for complete search history.

(56) References Cited

U.S. PATENT DOCUMENTS

| 4,455,280 A | 6/1984 | Shinohara et al. |
| 5,479,969 A | 1/1996 | Hardie et al. |

(Continued)

OTHER PUBLICATIONS

European Patent Office, International Search Report and Written Opinion of the International Searching Authority, International Application No. PCT/FI2011/050950, 12 pages, dated Jan. 27, 2012.

*Primary Examiner* — Lyle Alexander
*Assistant Examiner* — Bryan Kilpatrick
(74) *Attorney, Agent, or Firm* — Thompson Hine LLP (57) ABSTRACT

A method and apparatus for opening a reaction vessel having a body forming a volume for liquid, and a lid. In the method at least one reaction vessel is placed on a transport vehicle and the reaction vessel is positioned on the vehicle so that the vessel's rotation about its own axis is prevented. Then, the at least one reaction vessel is transferred on the vehicle and a guide rod, attached to the lid that is attached by a hinge to the reaction vessel, is pushed by the movement of the vehicle against a guide surface that forces the lid to turn on the hinge so that the lid is at least partially opened.

11 Claims, 7 Drawing Sheets

Related U.S. Application Data (60) Provisional application No. 61/408,059, filed on Oct. 29, 2010.

(51) Int. Cl.
*B65D 83/00* (2006.01)
*G01N 35/04* (2006.01)
*G01N 35/02* (2006.01)

(52) U.S. Cl.
CPC .... *B01L 2300/0841* (2013.01); *G01N 35/025* (2013.01); *G01N 2035/0405* (2013.01)

(56) References Cited

U.S. PATENT DOCUMENTS

| | | |
|---|---|---|
| 5,578,494 A | 11/1996 | Clark et al. |
| 5,628,962 A | 5/1997 | Kanbara et al. |
| 5,862,934 A | 1/1999 | Sattler et al. |
| 6,060,022 A | 5/2000 | Pang et al. |
| 6,265,225 B1 * | 7/2001 | Otto ............... B01L 3/50825 215/236 |
| 6,458,324 B1 | 10/2002 | Schinzel |
| 6,783,025 B2 * | 8/2004 | Lohn ............... B01L 3/50825 215/341 |
| 6,866,820 B1 * | 3/2005 | Otto ............... B65D 47/00 215/235 |
| 7,717,284 B2 | 5/2010 | Giusti |
| 9,821,313 B2 * | 11/2017 | Nuotio ............... B65D 83/00 |
| 2001/0028863 A1 | 10/2001 | Kitagawa |
| 2006/0228262 A1 | 10/2006 | Jacobs et al. |
| 2009/0117004 A1 | 5/2009 | Fritchie et al. |
| 2013/0118118 A1 | 5/2013 | Kubler et al. |

\* cited by examiner

REACTION VESSEL AND APPARATUS AND METHOD FOR OPENING AND CLOSING A REACTION VESSEL

CROSS REFERENCE TO RELATED APPLICATIONS

This application is a divisional of co-pending U.S. application Ser. No. 13/820,960, filed Apr. 12, 2013, which is a submission under 35 U.S.C. § 371 of International Application No. PCT/FI2011/050950, filed Oct. 28, 2011, which claims the benefit of U.S. Provisional Application Ser. No. 61/408,059, filed Oct. 29, 2010, the disclosures of which are incorporated herein by reference in their entireties.

FIELD OF INVENTION

The present invention relates to reaction vessels and an apparatus for opening and closing a lid of such reaction vessels in an automated chemical analyzer.

BACKGROUND OF INVENTION

In hospitals and laboratories, several chemical and diagnostic analyses are done by automatic analyzing equipment. The level of automation varies, but the present trend is to streamline the analyzing work as much as possible. As many more complicated analyzes must be done by highly educated laboratory personnel involving a lot of manual work, the productivity and throughput of a laboratory and individual analyzers has been low. If the automation rate is increased, more of the work can be performed automatically inside the automatic system without involvement of highly skilled personnel. Ideally, laboratory assistants simply load samples in racks into the analyzing apparatuses and laboratory chemists and biologists may concentrate on interpretation of the results and managing the operation of the laboratory. Such a system provides a good throughput combined with high certainty and quality of the work.

In order to enable the high rate of automation, many automated features are needed. One of the features is reliable management of sample liquids, reagents and other fluids needed for the operation of the analyzer. This involves sample vessels, reagent vessels and reaction vessels and means for transferring them within the automated analyzer. Another particularly important feature when the automated analyzer handles sensitive samples and/or utilizes volatile reagents is the use of a capped reaction vessel. However, capped reaction vessels introduce an additional mechanical problem when used on-board automated instrumentation: they must be automatically opened and closed. The following patent documents disclose some of the typical systems currently used in the art.

U.S. Pat. No. 6,866,820 shows a reaction vessel with a cap having an additional member for automatically opening it. In this system, the reaction vessel is opened and closed by moving a lid that is arranged on the top of the cap sideways with a probe. The probe is mounted on robotic or other automatic means for transferring a pipette. The vessel is opened by transferring the lid sideways by pushing it with the plunger. Herein the opening and closing of the lid are two separate operational steps needed when dispensing the liquid. Thus, the sideways moving lid and use of a movement of the pipette transferring means increased the time needed for pipetting considerably. The structure of the lid is also rather complicated. Various penetrable caps are also known. Problems relating to such caps are the force needed for penetration of the cap, mechanical damaging of the cap when penetrated, and most importantly, danger of contamination of the pipette needle. U.S. Pat. No. 7,717,284 discloses a flip cap that is operated by hand. Therefore it is not suitable for automated processes. However, these are good examples of the known reaction vessels.

U.S. Pat. No. 5,578,494 discloses chemical reagent storage vessels and tops that can be opened for distribution of reagents within.

SUMMARY OF THE INVENTION

In a first aspect, the invention relates to a reaction vessel having a lid that can be opened and closed.

One embodiment of the invention provides a reaction vessel having a lid made as one piece.

According to additional aspects and embodiments of the present invention, the invention provides a reaction vessel having a lid adapted for forced or guided opening and closing of the lid during automatic handling of the vessel.

According to one embodiment of the invention, the body of the reaction vessel has an inner surface defining an inner volume of the vessel and an opening at one end of the vessel. The outer surface of the vessel forms its outer contour and includes one or more features for locking the reaction vessel on a seat so that the vessel does not rotate around its own axis. The vessel has a lid that is attached by a hinge and includes a guide rod extending from the lid.

According to one embodiment of the invention, the reaction vessel has a gripping collar that surrounds the opening of the vessel. The gripping collar is preferably circular and has the same diameter as the lid of the vessel.

According to one embodiment of the invention, the vessel has a stopping collar under the gripping collar and the stopping collar has at least one modified surface part for preventing vessel rotation in a robot gripper the surface part being preferably two opposite flat faces at both sides of vessel.

In a second aspect, the invention relates to a method for opening and closing a lid of a reaction vessel.

One embodiment of the invention provides a method for moving a reaction vessel between two or more positions.

According to other aspects and embodiments of the present invention, the invention provides a method for forced or guided opening and closing of the lid of the reaction vessel.

According to one specific feature of the invention, the invention utilizes a single integral part for guiding the opening and closing movement.

The invention is based on rotating or transporting at least one reaction vessel on a transport vehicle, positioning the reaction vessel on the vehicle so that the reaction vessel does not rotate around its own axis, and pushing, by the movement of the vehicle, a guide rod attached to a lid that is attached by a hinge to the reaction vessel, against a guide surface that forces the rod and the lid to turn on the hinge so that the lid opens.

According to one embodiment of the invention, at least one reaction vessel is transported in a circular motion on a rotor disk, positioned on the rotor so that the reaction vessel does not rotate around its own axis, and a guide rod, attached to a lid that is attached by a hinge to the reaction vessel, is pushed by the rotational movement of the rotor disk against a guide surface that forces the rod and the lid to turn on the hinge so that the lid opens.

The closing of the lid may be based on guiding the lid against the guide surface to the opposite direction.

The closing of the lid may be based on guiding the lid against the guide surface to the original direction.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

DETAILED DESCRIPTION

Figure 1:
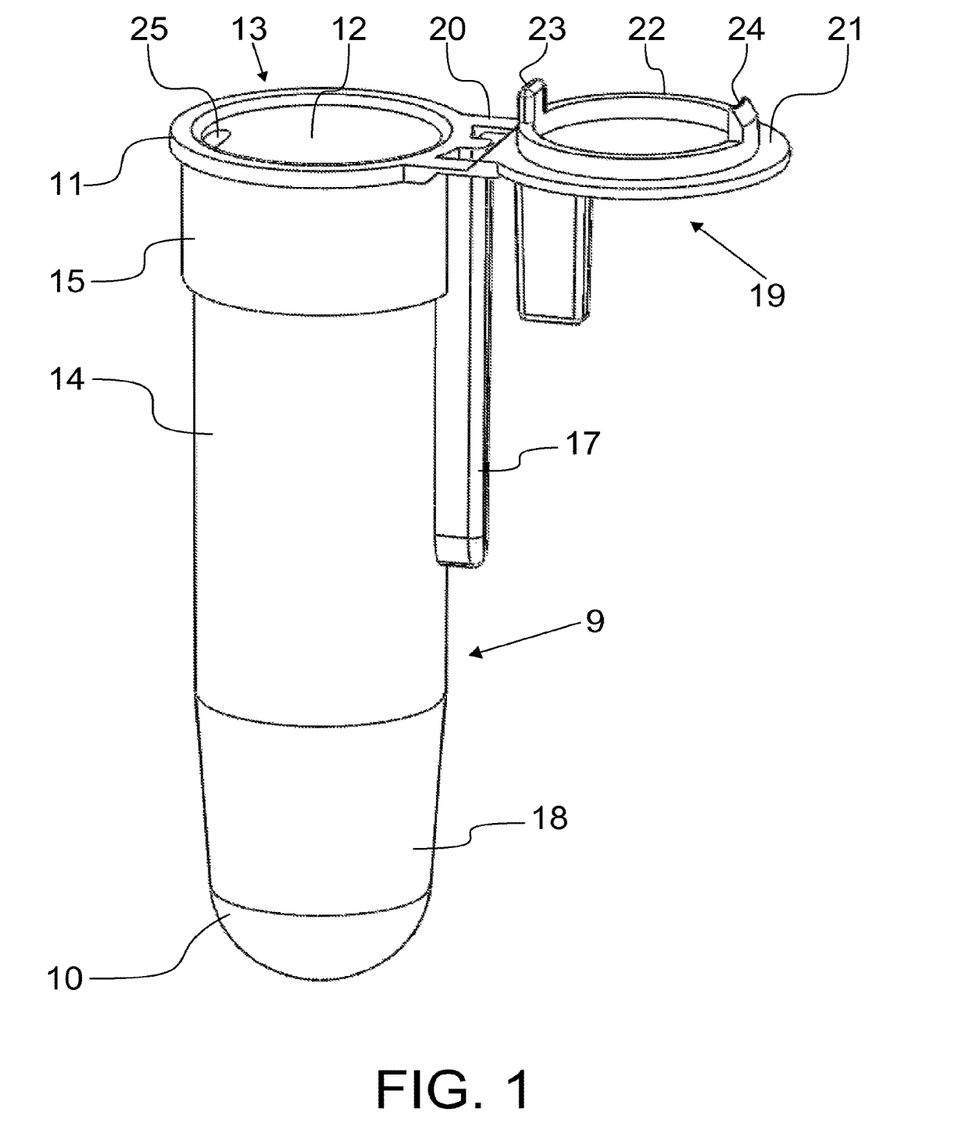
FIG. 1 is a side plan view of a reaction vessel in accordance with one embodiment of the present invention in an open position.
Figure 2:
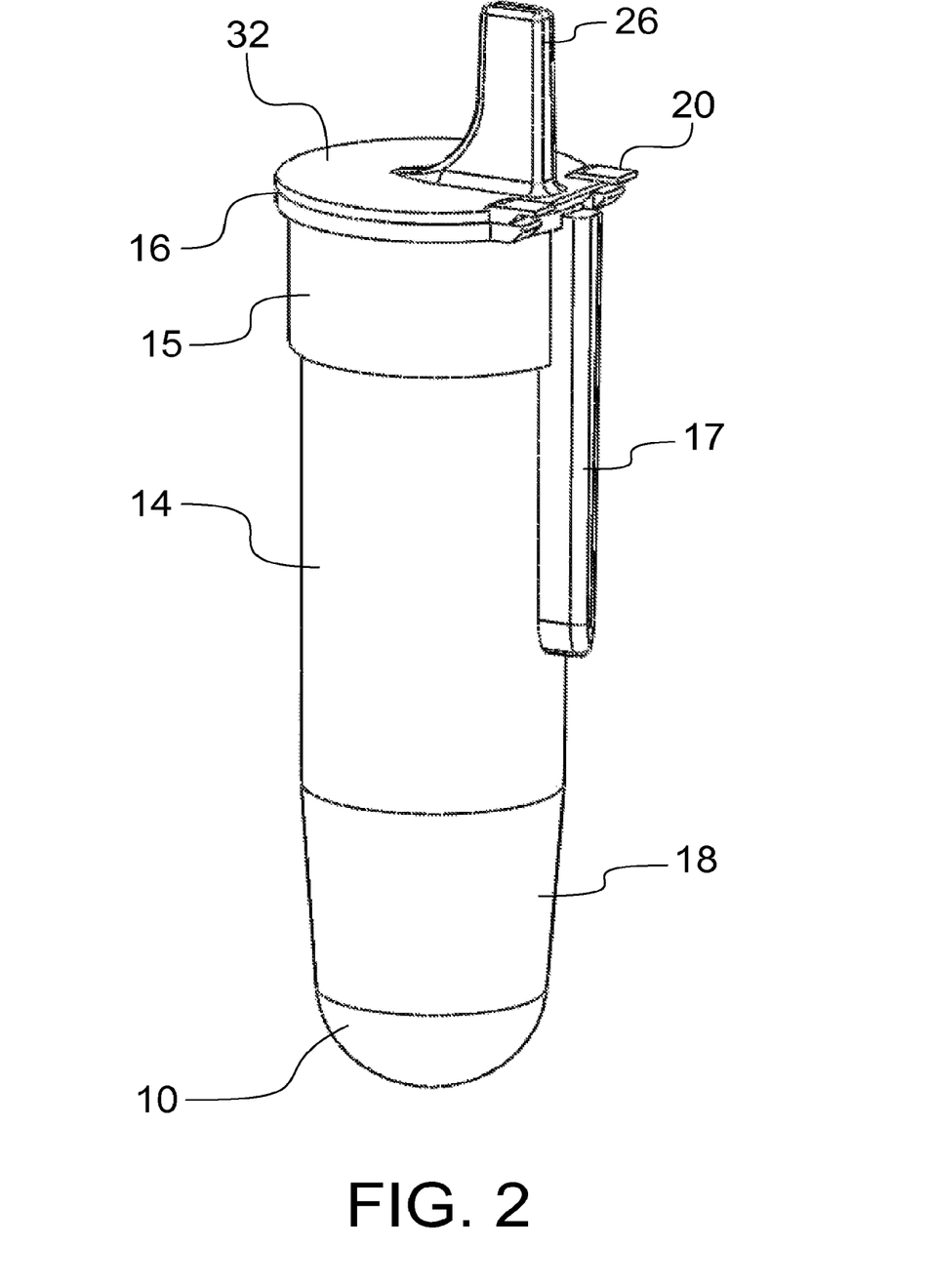
FIG. 2 is a side plan view of a reaction vessel in accordance with one embodiment of the present invention in a closed position.

One embodiment of the reaction vessel of the present invention is depicted in FIGS. 1 and 2. The reaction vessel 9 depicted in FIGS. 1 and 2 is a tube-like vessel having an inner surface 12 defining the inner volume of the vessel 9. The diameter of the reaction vessel 9 can be constant from the opening 13 to the closed end 10. Alternatively, the internal and/or external diameter of the reaction vessel 9 can vary along the longitudinal axis of the reaction vessel 9. For example, the internal and/or external diameter can decrease gradually or at one or more fixed points along the longitudinal axis of the reaction vessel 9.

The inner surface 12 of the reaction vessel 9 forms an opening 13 at one end of the vessel 9. The outer surface of the vessel 9 forms its outer contour and comprises a cylindrical body part 14 having a stopping collar 15 at the same end as the opening 13 of the vessel 9 and a gripping collar 16 at the same end and surrounding the opening 13 of the vessel 9. The diameter of the gripping collar 16 is preferably the same or smaller than the diameter of the lid 19 so that a gripper (not shown) can be pushed over the lid 19 and the collar 16 from above (from the side of the lid) to grip the edge of the gripping collar 16. One preferred cross section of the gripping collar 16 is circular and the lid 19 should have a complimentary form to the gripping collar 16 to ensure their compatibility. In this case, the jaws of a gripper used for handling the vessels 9 can be made as a sector of a circle having the same diameter.

Further, the outer surface of the reaction vessel 9 can include a guide rail 17 extending along all or a part of the outer surface of the reaction vessel 9 and parallel to its longitudinal axis.

The end of the reaction vessel 9 opposite to the opening is closed and, according to one embodiment, is herein formed of a conical taper 18 ending at a spherical closed end 10. The inner surface of the vessel 9 follows this form. The function of the spherical closed end 10 is to concentrate the last remaining liquid to the center of the vessel 9 wherein it can be collected by a needle of a pipette or other similar device.

One important feature of the reaction vessel 9 is the lid 19. The main body of the lid 19 is a circular plate having a closing surface 21 that is adapted to set on top of the opening 13 of the vessel 9 and the gripping collar 16 when the lid 19 is in a closed position. The circumference of the body of the lid 19 corresponds with the outer circumference of the gripping collar 16. According to one embodiment, the inside of the lid 19 includes a guide ring 22 with guide pegs, one 23 of which is on the side of the hinge 20 and the other 24 of which is on the opposite side of the lid 19. The peg 24 farther from the lid 19 can be beveled.

The lid 19 comprises a hinge 20 connecting it to the body of the reaction vessel 9. According to one embodiment, the hinge 20 connects the lid 19 to the gripping collar 16 on the body of the vessel 9. On the inner surface 12 of the reaction vessel 9 and opposite to the hinge 20 is a knob 25 that is arranged to contact and engage the beveled peg 24. These elements may be arranged to opposite parts, so that peg 24 includes the knob 25 and the inner surface includes a corresponding dent (not shown).

The edge of the inner surface 12/opening 13 of the reaction vessel 9 is also beveled to lead the guide ring 22 inside the opening 13. When closed, the beveled peg 24 and knob 25 hold the lid 19 closed and the lid 19, guide ring 22 and the opening 13 can be dimensioned so that the required level of tightness is achieved between the components. The knob 25 may be replaced by a groove or left out if sufficient closure is otherwise achieved. The lid 19 can be liquid tight, gas tight or just provide a sufficient closure of the vessel 9 that prevents excessive evaporation.

The outer surface of the main body of the lid 19 comprises a circular flat surface 32 and a guide rod 26 extending away therefrom. According to one embodiment, the guide rod 26 is arranged between the center point of the lid 19 and the hinge 20 connecting it to the reaction vessel 9. The purpose of the guide rod 26 will be clarified below. The guide rod 26 extends preferably upwards from the flat surface 32 of the lid 19 and so that it does not reach over the circumferential edge of the lid 19. This requirement is simply reasoned by the fact that if the guide rod 26 extends horizontally further than the other dimensions of the vessel 9, the vessel 9 needs more space sideways.

The reaction vessel 9 described herein is only one possible embodiment that can be used for implementation of the invention. For example, the guide rail 17 can be replaced by any form made on the outer surface of the vessel 9 that prevents rotation of the vessel 9. Examples of alternative forms made on the outer surface of the vessel 9 include two or more guide rails 17, a rectangular or other angular form on the outer surface of the vessel 9, or one or more grooves within the outer surface of the vessel 9. Further, the collars 15, 16 can be formed to perform the desired function. The collars have preferably a circular cross section and are formed as cylinders. However, rectangular, diamond shaped or other polygonal shape of cross section can also be used. The vessel 9 itself may have any desired inner or outer design; so long as it has a volume for liquid and an opening 13 that can be closed by a lid 19.

The hinge 20 of the lid 19 can be made as a separate piece and/or using a separate material or simply be formed as a single piece of the same material as the vessel 9 and lid 20 themselves. Preferably, the lid 19 and the vessel 9 are made as a single piece, for example by injection molding.

In this embodiment, the flat surface 32 of the lid 19 operates as one guide surface and the guide rod 26 as another guide surface. Alternatively, there may be separate guide surface on the flat surface 32 of the lid 19 and the guide rod 26 may have a different form. One example of this will be described below. The relative placement of the guide rod 26 in view of the lid 19 and the hinge 20 may vary.

One especially preferred embodiment that illustrates some of the variable features mentioned above, is shown in FIGS. 6 and 7.

Figure 6:
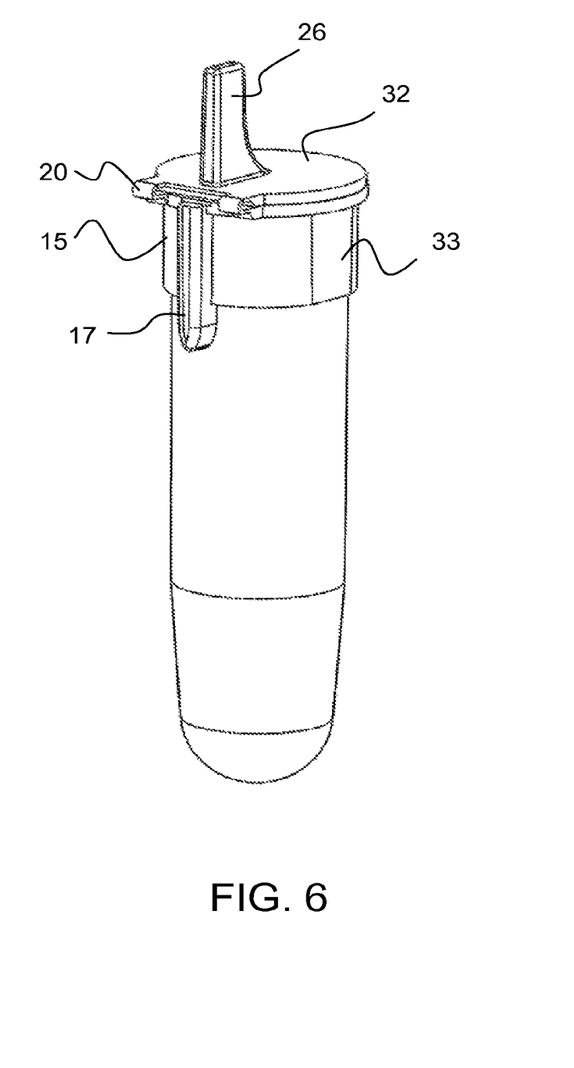
FIG. 6 is a side plan view of reaction vessel in accordance with another embodiment of the present invention in a closed position.
Figure 7:
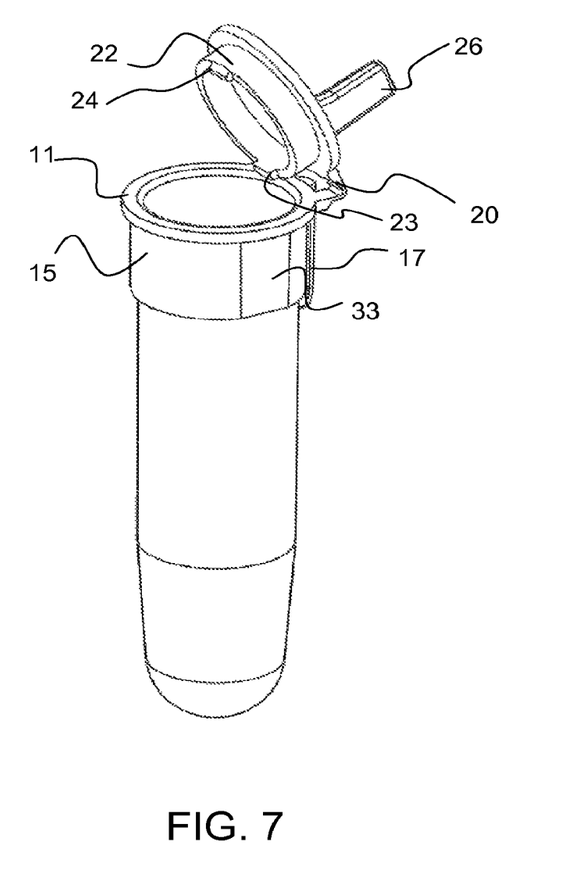
FIG. 7 is a side plan view of a reaction vessel in accordance with another embodiment of the present invention in an open position.

In this embodiment the stopping collar 15 has two opposite flat faces 33, one on each side of the vessel, for preventing vessel rotation in a robot gripper. Instead of flat faces, at least one modified surface part such as a groove, toothing, rifling or a bulge can be used. These can be set pairwise or in other suitable formation around the stopping collar 15.

The inside of the lid 19 includes a guide ring 22 with guide pegs, one 23 of which is on the side of the hinge 20 and the other 24 of which is on the opposite side of the lid 19. The peg 24 farther from the lid 19 can be beveled. Herein the guide ring 22 is extended to a sealing skirt in order to improve tightness and sealing ability. The sealing ability can be adjusted by adapting the tolerances between the surfaces and the length of the sealing skirt to the demands of the fluid or other substance handled in the vessels. It can even be contemplated that the guide ring or sealing skirt 22 is provided with a sealing element, for example an O-ring. The drawbacks of adding extra sealing element is increased complicity and costs.

Further, the guide rail 17 extending along a part of the outer surface of the reaction vessel 9 and parallel to its longitudinal axis is herein shortened to fit it better in an intermediate storage. It is evident that the dimensions of the guide fin shall be adapted to dimensions of storage and handling positions.

The purpose of closing the reaction vessel 9 is, firstly, to prevent evaporation and enrichment of a liquid therein. Secondly, closing of the vessel 9 prevents contamination of the contents and prevents spilling if the vessel 9 is dropped. Further, closing also prevents spilling during vortexing mixing and movements by robotics. The operation of the reaction vessel 9 and the opening and closing apparatus is described below to show how opening and closing of the reaction vessel 9 is achieved according to the invention.

Figure 3:
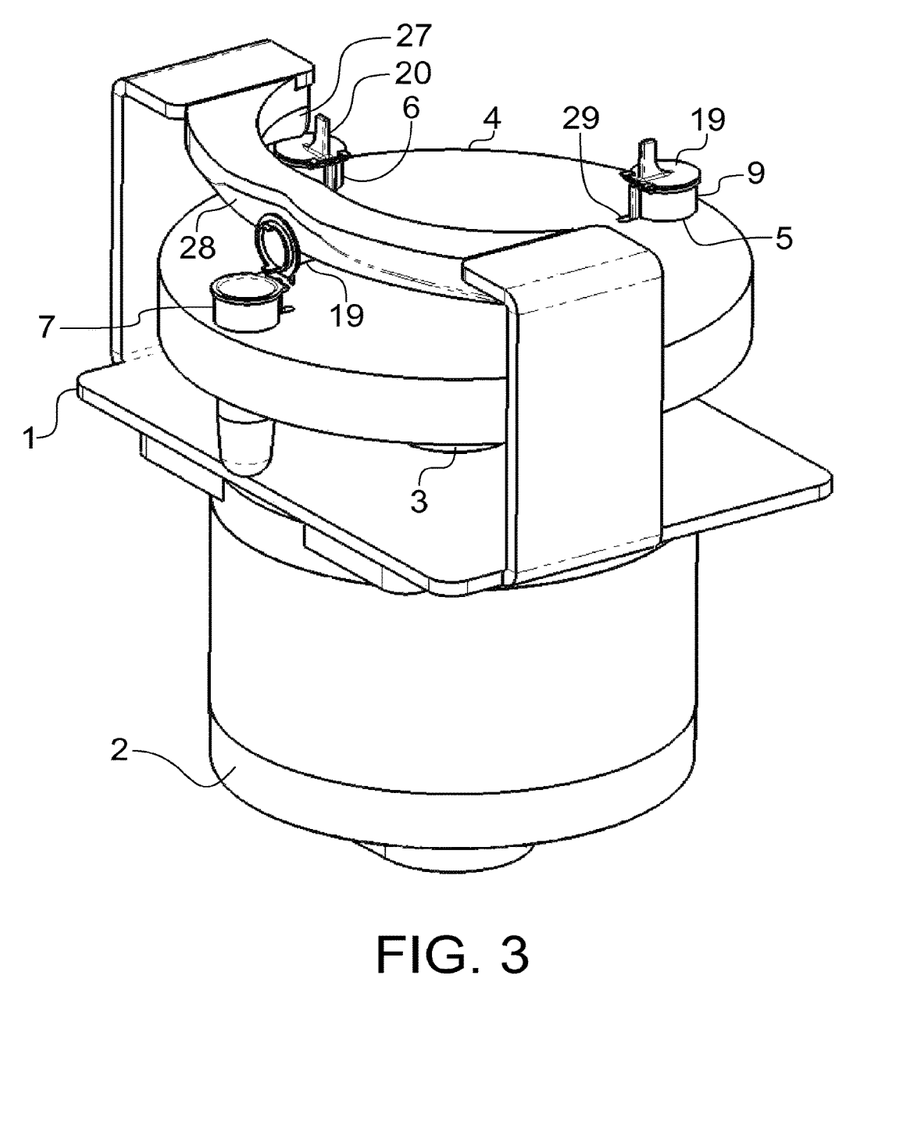
FIG. 3 is a side plan view of a reaction vessel opening and closing device according to one embodiment of the present invention in a first position during operation.
Figure 4:
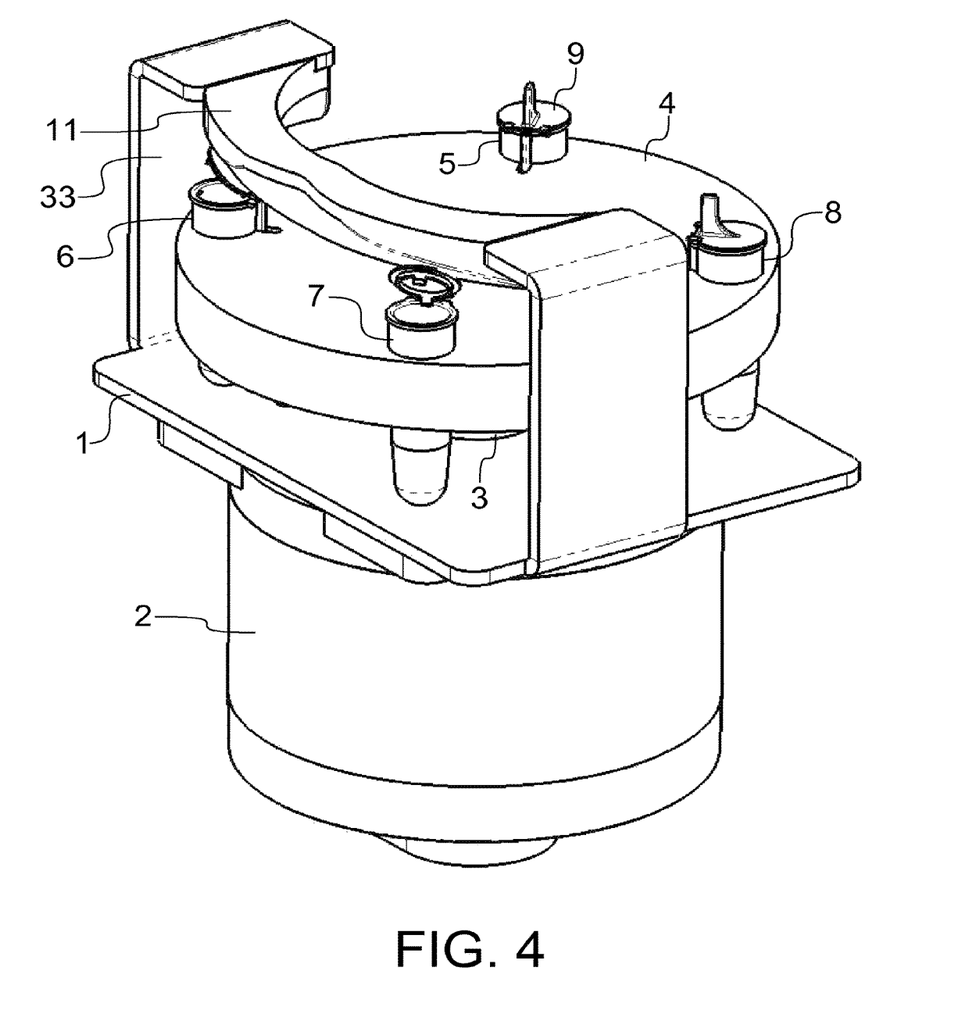
FIG. 4 is a side plan view of the device of FIG. 1 in a second position during operation.

FIGS. 3 and 4 show an embodiment of the reaction vessel opening and closing apparatus invention. This apparatus is built on a base plate 1 having an electric motor 2 mounted thereto. The motor 2 can be a step motor or any other actuator that can be driven between at least two angular positions. The axle 3 of the motor 2 extends through the base plate 1. A rotor disk 4 is mounted at the end of the axle 3 and has four seats 5, 6, 7, 8 for receiving reaction vessels 9. The seats 5, 6, 7, 8 are formed to accommodate the outer surface of the reaction vessels 9 and the center point of each reaction vessel 9 is placed in a position the same radius from the center of the rotor disk 4. Thus, when the rotor disk 4 is rotated, the seats 5, 6, 7, 8 and vessels 9 set in them travel the same circular path. From the base plate 1 extends, on the opposite side to the motor 2 and around the perimeter of the rotor disk 4, two brackets 33, which are mounted in a stationary position over the rotor disk 4. A stationary guide piece 11 is mounted between the brackets 33.

The opening and closing operation of the device depicted in FIGS. 1 and 2 is based on rotational movement of the rotor disk 4 in concert with the guiding action of the guide piece 11. The rotor 4 may rotate in either a clockwise or counterclockwise direction, or alternate between both directions. According to the embodiment depicted in FIGS. 3 and 4, the rotor 4 rotates in a counterclockwise direction.

In the embodiment depicted in FIGS. 3 and 4, the rotor disk 4 has four seats 5, 6, 7, 8 for accommodating up to four reaction vessels 9. Each of these seats are placed at regular angular intervals on the rotor disk 4 at the same radius from the center of the rotor disk 4. Each seat 5, 6, 7, 8 has a guide slot 29. When reaction vessels 9 are placed in the seats 5, 6, 6, 8, the guide rails 17 of the vessels sit in the guide slots 29 within the seats 5, 6, 7, 8, setting and locking the rotational position of the vessels 9, preventing the vessels 9 from rotating about their own axis.

In the vertical direction, the stopping collar 15 of the reaction vessel 9 sets the vessel 9 to its correct height within the seat 5 relative to the surface of the rotor disk 4 and the guide piece 11. This height placement is important for the operation of the opening and closing features and, in an automated analyzer, for facilitating aspiration of liquid from the vessel 9. When the vessels 9 are placed within the seats 5, 6, 6, 8, the hinges 20 of the vessels 9 point to the center of the rotor disk 4. When the rotor disk 4 is rotated, each of the up to four vessels 9 moves along the same circular path.

As depicted in FIG. 3, seat 5 is in a loading position and is able to accept a reaction vessel 9. In this position, the vessel 9 can be removed from or placed on the rotor 4. When the vessel 9 is placed in the loading position, the vessel 9 is closed. In order to access the contents of the vessel 9, the lid 19 of the vessel 9 must be opened. Simultaneously, the vessel 9 has to be moved to an accessing position where a needle or pipette (not shown) can be inserted into the vessel 9 to access the contents of the vessel 9 and aspirate or dispense the required amount of liquid from or into the vessel 9. With reference to FIG. 3, seat 7 is located in the accessing position.

The guide piece 11 includes one continued curved surface which touches either or both the guide rod and top of the lid in a proper way. Surfaces 27 and 28 are not separate surfaces) but comprise two sections, a first guide surface 27 positioned on the vertical surface of the guide piece 11 closest to the center of the rotor 4, and a second guide surface 28 positioned on the vertical surface of the guide piece 11 farthest from the center of the rotor 4. Each of the first and second guide surfaces 27, 28 are designed to engage the lid 19 and the associated guide rod 26 to open and close the lid 19 as the vessel 9 travels across the guide piece 11.

Opening of the lid 19 starts when the rotor disk 4 is rotated counterclockwise from the loading position (seat 5 in FIG. 3) and the vessel 9 arrives to the engagement point, the position where seat 6 is located in FIG. 13 When the vessel 9 continues to rotate in a counterclockwise direction past this engagement point, the guide rod 26 of the lid 19 engages with the first guide surface 27 of the guide piece 11.

The portion of the first guide surface 27 of the guide piece 11 located closest to the brackets 10 is curved to be so far away from the center of the rotor disk 4 that the upstream end of the surface of the first guide surface 27 may permit the guide rod 26 of the vessel 9 to pass by the guide piece 11 without engaging or moving the guide rod 26.

In the direction of the rotation, counterclockwise according to the depicted embodiment, the first guide surface 27 gradually curves inwards away from the center of the rotor disk 4. Also, at the engagement point (seat 6 in FIG. 3) the first guide surface 27 is essentially vertical, corresponding to the form of the guide rod 26 of the vessel 9 when the lid 19 is in a closed position on the side of the guide rod surface that points outwards from the center point of the rotor blade 4 and the hinge 20 of the vessel 9. From the engagement point, the first guide surface 27 turns gradually inwards from a vertical position towards a horizontal position so that the first guide surface 27 is almost horizontal at the point where the vessel 9 reaches the accessing position, located at seat 7 in FIG. 1. Thus, the first guide surface 27 pushes the guide rod 26 and its associated vessel lid 19 open by pushing the guide rod 26 towards the center of the rotor disk 4 and downwards, from a vertical position to a horizontal position directed towards the center of the rotor disk 4.

Simultaneously, the second guide surface 28 must provide sufficient space to allow the lid 19 of the vessel 9 to rise upwards as the guide rod 26 is being lowered. This is possible by simply forming the second guide surface 28 of the guide piece 11 so that there is enough space for the lid 19 to rise. If more constrained guidance is desired, the second guide surface 28 may start with a horizontal surface at the portion of the guide piece 11 located closest to the brackets 10 and gradually curve outwards away from the center of the rotor disk 4 to allow the lid 19 to rise. This form of the second guide surface 28 is depicted in FIGS. 3 and 4.

In order to close the lid 19, the second guide surface 28 of the guide piece 11 is curved outwards from the center of the rotor disk 4 and a vertical position towards a horizontal position so that the second guide surface 28 glides on the flat surface 32 of the lid 19 and presses the lid 19 downward and closed. The lid 19 can be pressed closed by the guide piece 11 or the guide piece 11 can include a structure that draws the lid 19 closed. According to various embodiments, the second guide surface 28 can include a flexible surface, an extended spring, or even a powered pusher to be certain the lid is closed. The force needed to close the lid 19 is dependent on how tight the lid 19 has to be, for example liquid or gas tight seals are inherently tighter than a lid 19 that just prevents some evaporation and access of solid contaminants. One advantage of a guide piece 11 wherein the guide surfaces 27, 28 have been formed on the outer surface of the guide piece 11 is that the guide piece 11 can be made completely smooth. Therefore it is easy to keep the guide surfaces 27, 28 clean and they are less likely to collect or distribute contaminants.

Figure 5:
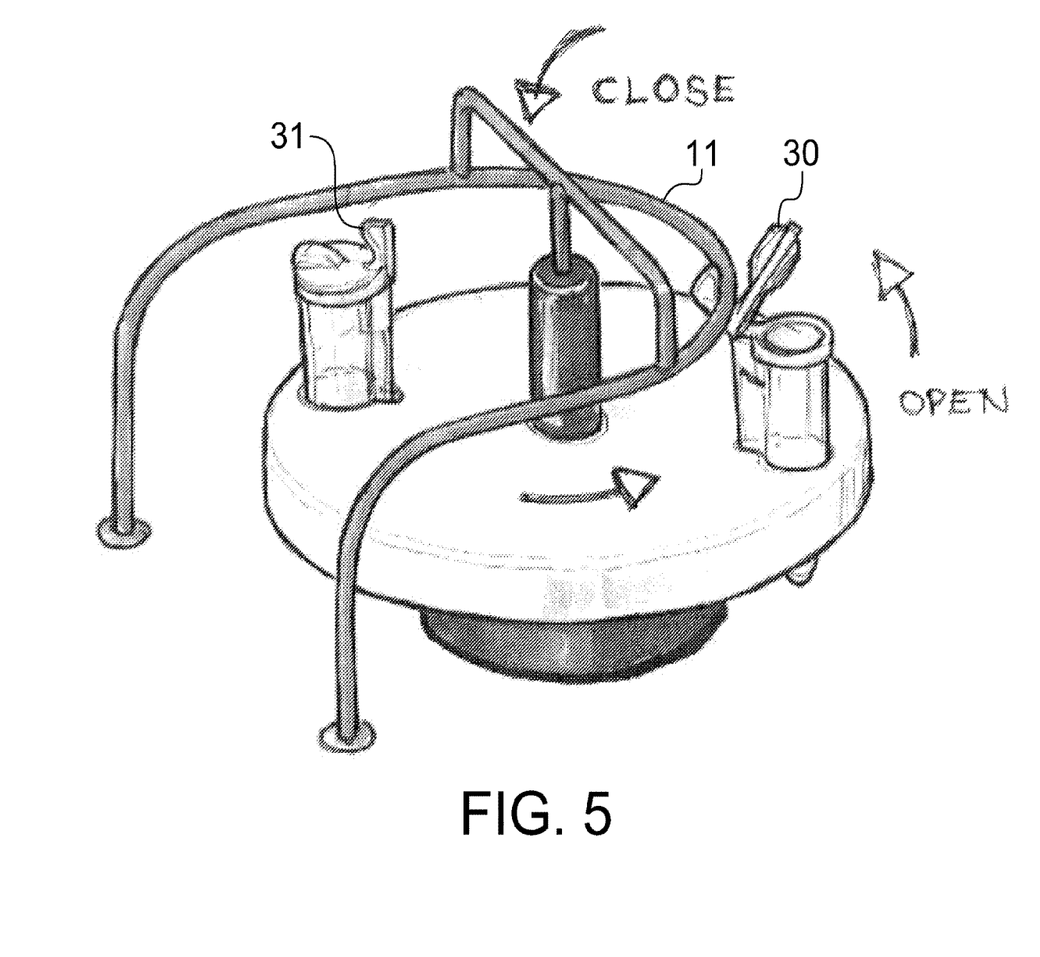
FIG. 5 is a side plan view of an alternative embodiment of the reaction vessel opening and closing device according to the invention.

FIG. 5 discloses an alternative embodiment of the opening and closing apparatus of the invention. Herein, the guide piece has been replaced by a round guide wire 11 that has been curved to form the guide. Also, the reaction vessels shown in FIG. 5 are somewhat different than the embodiments of the reaction vessels 9 depicted in FIGS. 1 and 2 and described above. The lids of the reaction vessels depicted in FIG. 5 include a push ridge 30 and the guide rod is formed as a hook 31. As can be seen from FIG. 5, the guide wire 11 operates in a same way as the guide piece 11 of the previous embodiment by engaging the hook 31, drawing the hook towards the center of the rotor and pushing downwards to open the lid, and, afterwards, closing the lid by pushing the lid on top of the push ridge downward and away from the center of the rotor. While this is a very simple embodiment, in practice a single guide piece formed of one part is easier to make and provides more possibilities to vary the guide surface(s).

As can be readily deducted, the guide piece, guide wire or other guide element can take various different forms. Naturally, the guide rod 26 of the lid 19 must be designed to accommodate the design of the guide piece 11. First, the guide rod 26 does not have to extend upwards from the lid 19; the guide rod 26 can also extend from the side of the lid 19 within the scope of the invention, but then the vessels 9 would require more space sideways. Such an embodiment would not be desirable in most cases. The guide piece 11 can also be positioned on the outside perimeter of the rotor disk 4 so that the lid 19 is pushed towards the edge of the rotor 4 when opened. However, this may hinder accessibility of the opening 13 of the vessel 9 to the pipette.

One embodiment for guiding the opening of the lid 19 of the vessel 9 might be a guide groove carved into the guide piece 11. This guide groove might be traced by a pin-like round guide rod 26.

The rotor disk 4 may have any number of seats 5 for vessels 9 from one to several, and opening and closing may be done several times during one full rotation around the rotor 4. It can even be contemplated that the rotor disk 4 is rotated continuously, but then the processes of loading vessels, removing vessels and taking samples or other liquids from the vessels might be more difficult, at least at higher speeds.

Instead of rotary movement, the reaction vessels 9 can be transferred along a linear or curved path. The path may be a track having a finite length or it can be an endless track. In this case, the reaction vessels 9 need a transport vehicle that transfers the vessels along the track to move the lids 19 of the vessels 9 between the open and closed positions. The guide surface must follow the path of the track and it may be divided into separate closing and opening surfaces. It can be further contemplated that there are several opening and closing positions along the track. The track herein is used to describe any means for providing guided transport of a vehicle.

According to another embodiment, the reaction vessel 9 may include a spring hinge 20 or other means for automatically closing the lid. In this embodiment, the opening and closing apparatus may be used only for opening the lid 19 of the vessel 9.

Thus, while there have been shown and described and pointed out fundamental novel features of the invention as applied to a preferred embodiment thereof, it will be understood that various omissions and substitutions and changes in the form and details of the method and device may be made by those skilled in the art without departing from the spirit of the invention. For example, it is expressly intended that all combinations of those elements and/or method steps which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. A reaction vessel that can be opened and closed, the reaction vessel comprising:
   a body forming a volume for liquid and an opening in a top end of the body,
   a lid for closing the opening,
   a guide rail on an outer surface of the body for positioning the reaction vessel on a seat so that the reaction vessel's rotation about its own axis is prevented,
   a hinge attaching the lid to the body, and
   a guide rod attached to the lid and extending therefrom.

2. The reaction vessel according to claim 1, wherein a force can be applied to push said guide rod so that the guide rod and the lid turn on the hinge to open said lid.

3. The reaction vessel according to claim 1, wherein the guide rod extends outwards from the outer surface of said lid so that the guide rod remains horizontally within the edge of the lid when the lid is in a closed position.

4. The reaction vessel according to claim 3, wherein the guide rod is mounted on the lid between said hinge and a center point of said lid.

5. The reaction vessel according to claim 1, wherein the body, the lid and the hinge are made of a single piece of material.

6. The reaction vessel according to claim 1, wherein the body further comprises a gripping collar and a stopping collar, wherein the stopping collar is under the gripping collar, and wherein the stopping collar has at least one modified outer surface part for preventing vessel rotation in a robot gripper, the outer surface part being preferably two opposite flat faces, one on each outer side of the body.

7. The reaction vessel according to claim 2, wherein the guide rod extends outwards from the outer surface of said lid so that the guide rod remains horizontally within the edge of the lid when the lid is in a closed position.

8. The reaction vessel according to claim 2, wherein the vessel body, the lid and the hinge are made of a single piece of material.

9. The reaction vessel according to claim 1, wherein the seat comprises a guide slot.

10. The reaction vessel according to claim 9, wherein the guide rail sits in the guide slot of the seat when the reaction vessel is placed in the seat.

11. The reaction vessel according to claim 1, wherein the guide rail is tapered at its lower end.

\* \* \* \* \*